United States Patent
Borges et al.

(10) Patent No.: US 9,970,862 B2
(45) Date of Patent: May 15, 2018

(54) REFLECTIVE TAG AND POLARIZED LIGHT SENSOR FOR TRANSMITTING INFORMATION

(71) Applicant: International Business Machines Corporation, Armonk, NY (US)

(72) Inventors: Gabriel P. Borges, Sumaré (BR); Claude Falbriard, Cananeia (BR); Grant D. Miller, Arvada, CO (US); Nader M. Nassar, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 613 days.

(21) Appl. No.: 14/332,426

(22) Filed: Jul. 16, 2014

(65) Prior Publication Data
US 2016/0018318 A1   Jan. 21, 2016

(51) Int. Cl.
*G01N 21/25* (2006.01)
*G01J 3/46* (2006.01)
(Continued)

(52) U.S. Cl.
CPC ............... *G01N 21/25* (2013.01); *G01J 3/46* (2013.01); *G01N 21/21* (2013.01); *G01N 21/23* (2013.01);
(Continued)

(58) Field of Classification Search
CPC ........ G01N 21/21; G01N 21/23; G01N 21/25; G01N 21/29; G01N 21/293; G01N 21/55;
(Continued)

(56) References Cited

U.S. PATENT DOCUMENTS 3,443,072 A  *  5/1969  Mori .................... B61L 25/041
                                                      235/454
4,682,016 A      7/1987  Inoue
(Continued)

FOREIGN PATENT DOCUMENTS

| CA | 2790925 A1 | 9/2011 |
| CN | 102896892 A | 1/2013 |
| JP | 2007101277 A | 4/2007 |

OTHER PUBLICATIONS

Desplan, Claude, "Color and polarized light vision: The *Drosphila* retinal mosaic", pp. 1-13, provided by inventor in disclosure dated Sep. 22, 2013, <http://silverdialogues.fas.nyu.edu/docs/IO/24390/Desplan_Silver_Essay.pdf.

(Continued)

*Primary Examiner* — Gordon J Stock, Jr.
(74) *Attorney, Agent, or Firm* — David Zwick; Andrew M. Calderon; Roberts Mlotkowski Safran Cole & Calderon, P.C.

(57) ABSTRACT

Polarized light characteristics are detected and mapped to an application, such as product identification. A process of reflecting a directed light emission through a polarizing filter, and sensing the processed light emission having particular characteristics is provided. The characteristics of the sensed light emission is associated with a "color code" that is cross-referenced within a database of color codes.

20 Claims, 3 Drawing Sheets

(51) Int. Cl.
    *G01N 21/55* (2014.01)
    *G01N 21/21* (2006.01)
    *G01N 21/23* (2006.01)

(52) U.S. Cl.
    CPC ........ *G01N 21/55* (2013.01); *G01J 2003/466* (2013.01); *G01N 2201/10* (2013.01); *G01N 2201/12* (2013.01)

(58) Field of Classification Search
    CPC ... G01N 2201/10; G01N 2201/12; G01J 3/46; G01J 3/463; G01J 2003/466; G01J 4/00; Y10S 428/916; H01Q 15/14; H01Q 15/148; H01Q 15/22; H01Q 15/23; H01Q 15/24; H01Q 15/242; H01Q 15/244; H01Q 15/246; H01Q 15/248; G09F 3/00; G09F 3/0291; G09F 3/0294; G09F 3/0297; G09F 3/0376; G09F 2003/0212; G02B 5/0825; G02B 5/0833; G02B 5/0841; G02B 5/085; G02B 5/0858; G02B 5/0875; G02B 5/1833; G02B 5/22; G02B 5/223; G02B 5/226; G02B 5/23; G02B 5/26; G02B 5/265; G02B 5/285; G02B 5/286; G02B 5/287; G02B 5/30; G02B 5/3008; G02B 5/3016; G02B 5/3033; G02B 5/3041; G02B 5/305; G02B 5/3066; G02B 5/3083; G02B 5/32; B82Y 20/00; B82Y 30/00; B61L 25/041; H04N 2201/3269; H04N 2201/327; H04N 1/32144; H04N 1/32149; H04N 1/3229; H04N 1/32352; H04N 1/32288; H04N 1/32299; H04N 1/32304; H04N 1/32309; H04N 1/32342; G06T 7/0004; G06Q 30/018; G06Q 30/0185; B07C 5/3412; B07C 5/342; G06K 19/06009; G06K 19/06018; G06K 19/06028; G06K 19/06037; G06K 19/06046; G06K 19/06084; G06K 19/06093; G06K 19/06131; G06K 19/0614; G06K 2019/06225; G06K 2019/06253; G06K 2019/06262; G06K 2209/00; G06K 2209/17; G06K 2209/19; G06K 2209/21; G06K 2209/23; B42D 25/23; B42D 25/29; B42D 25/30; B42D 25/328; B42D 25/351; B42D 25/36; B42D 25/364; B42D 25/373; B42D 25/378; B42D 25/391; B42D 2033/00; B42D 2033/03; B42D 2033/06; B42D 2033/10; B42D 2033/13; B42D 2033/18; B42D 2033/20; B42D 2033/26; B42D 2033/30; B42D 2035/34; B42D 2035/36
    See application file for complete search history.

(56) References Cited

U.S. PATENT DOCUMENTS

| | | | | |
|---|---|---|---|---|
| 4,901,364 A | * | 2/1990 | Faulkerson | G06K 9/228 341/23 |
| 5,256,865 A | * | 10/1993 | Wike, Jr. | G06K 7/10861 235/462.15 |
| 5,974,150 A | * | 10/1999 | Kaish | G06K 19/086 283/85 |
| 6,434,561 B1 | * | 8/2002 | Durst, Jr. | H04N 1/33323 |
| 7,446,303 B2 | | 11/2008 | Maniam et al. | |
| 8,169,523 B2 | | 5/2012 | Itonaga | |
| 8,218,857 B2 | | 7/2012 | Moriyama et al. | |
| 8,478,035 B2 | | 7/2013 | Fowler | |
| 2005/0024626 A1 | * | 2/2005 | Faris | B42D 25/29 356/71 |
| 2005/0038756 A1 | * | 2/2005 | Nagel | G06K 19/086 705/76 |
| 2006/0001739 A1 | * | 1/2006 | Babayoff | A61B 1/00009 348/49 |
| 2006/0027662 A1 | * | 2/2006 | Baradi | G06K 7/12 235/469 |
| 2006/0086528 A1 | * | 4/2006 | Clare | G06K 19/06018 174/122 G |
| 2006/0097997 A1 | | 5/2006 | Borgaonkar et al. | |
| 2007/0220537 A1 | * | 9/2007 | Benedikt | G11B 7/24 720/719 |
| 2012/0067955 A1 | * | 3/2012 | Rowe | G06K 7/12 235/454 |
| 2013/0256415 A1 | * | 10/2013 | Callegari | B42D 25/29 235/454 |
| 2016/0247007 A1 | * | 8/2016 | Herrmann | G01N 21/21 |

OTHER PUBLICATIONS

Marshall, et al., "The Compound Eyes of Mantis Shrimps (Crustacea, Hoplocarida, Stomatopoda). I. Compound Eye Structure: The Detection of Polarized Light", Philosophical Transactions of the Royal Society of London, Series B: Biological Sciences, vol. 334, No. 1269, Published Oct. 29, 1991, pp. 33-56, Online ISSN: 1471-2970, Copyright © The Royal Society 2014, <http://rstb.royalsocietypublishing.org/content/334/1269/33>.

Park, et al., "From Detecting to Recognizing Color Codes", ISBN 89-5519-129-4, Feb. 20-22, 2006, ICACT2006, pp. 2228-2230, <http://ieeexplore.ieee.org/xpl/articleDetails.jsp?tp=&arnumber=1626047&searchWithin%3Dcolor+tag%26queryText%3Ddevice+for+.QT.color+code.QT.+scanning>.

"All Weather (NEMA-6P) True RGB Color Detector and light intensity Probe", AtlasScientific Biology Technology, ENV-RGB V 1.6, pp. 1-11, Copyright © Atlas Scientific LLC, <https://www.atlas-scientific.com/_files/_datasheets/_sensor/ENV-RGB.pdf>. no date.

"Researchers Discover a New Way Fish Camouflage Themselves in The Ocean", The University of Texas at Austin, College of Natural Sciences, Jun. 3, 2013, <http://cns.utexas.edu/news/fish-camouflage>.

"222—Light reflected from a specimen surface changes the state of polarization", YouTube Video, Physics-Animations.com, Published on May 26, 2013, <http://www.youtube.com/watch?v=IE7R91yOrfk>.

"Polarization", The Physics Hypertextbook, © 1998-2014 Glenn Elert, pp. 1-4, <http://physics.info/polarization/>.

"Extraordinary Vision: Polychromacity, Polarization in Mantis Shrimp", Science Tumbled, posted on Apr. 15, 2013, pp. 1-6, <http://science.tumblr.com/post/48036499588/extraordinary-vision-polychromacity-polarization-in>.

"Six challenges for molecular nanotechnology", Soft Machines, posted on Dec. 18, 2005, <http://www.softmachines.org/wordpress/?p=175>.

"Mantis Shrimp", Wikipedia, the free encyclopedia, past last modified Apr. 4, 2014, <http://en.wikipedia.org/wiki/Mantis_shrimp>.

"Panasonic Developing Groundbreaking High-Sensitivity Sensors Featuring Color Micro-Splitters Instead of Traditional Color Filters", SLR Lounge, Feb. 4, 2013, pp. 1-7, © 2014, <http://www,slrlounge.com/panasonic-micro-splitter-sensors>.

* cited by examiner

REFLECTIVE TAG AND POLARIZED LIGHT SENSOR FOR TRANSMITTING INFORMATION

FIELD OF THE INVENTION

The present invention relates generally to the field of information transmission, and more particularly to color-coded information systems.

BACKGROUND OF THE INVENTION

Polarization is a property of certain waves that they oscillate with more than one orientation. Electromagnetic waves, such as light, exhibit polarization. In a light wave, both the electric field and magnetic field are oscillating, but in different directions. The oscillation of these fields may be in a single direction (linear polarization), or the field may rotate at the optical frequency (circular, or elliptical, polarization). Where the field rotates, the direction of rotation, and thus the specified polarization, may be either clockwise or counter clockwise.

The most common optical materials (such as glass) are isotropic, meaning they simply preserve the polarization of a wave, but do not differentiate between polarization states. Some classes of materials known as birefringent, or optically active, generally modify a wave's polarization, or affect wave propagation passing through the material.

SUMMARY

In one aspect of the present invention, a method, a computer program product, and a system includes: detecting a first light emission having a first set of characteristics reflected from a target area on a surface of an object, and determining a color code based, at least in part, on the first light emission. At least the detecting and determining steps are performed by computer software running on computer hardware. The first light emission is a polarized reflection from the target area of a second light emission having a second set of characteristics.

DETAILED DESCRIPTION

Figure 1:
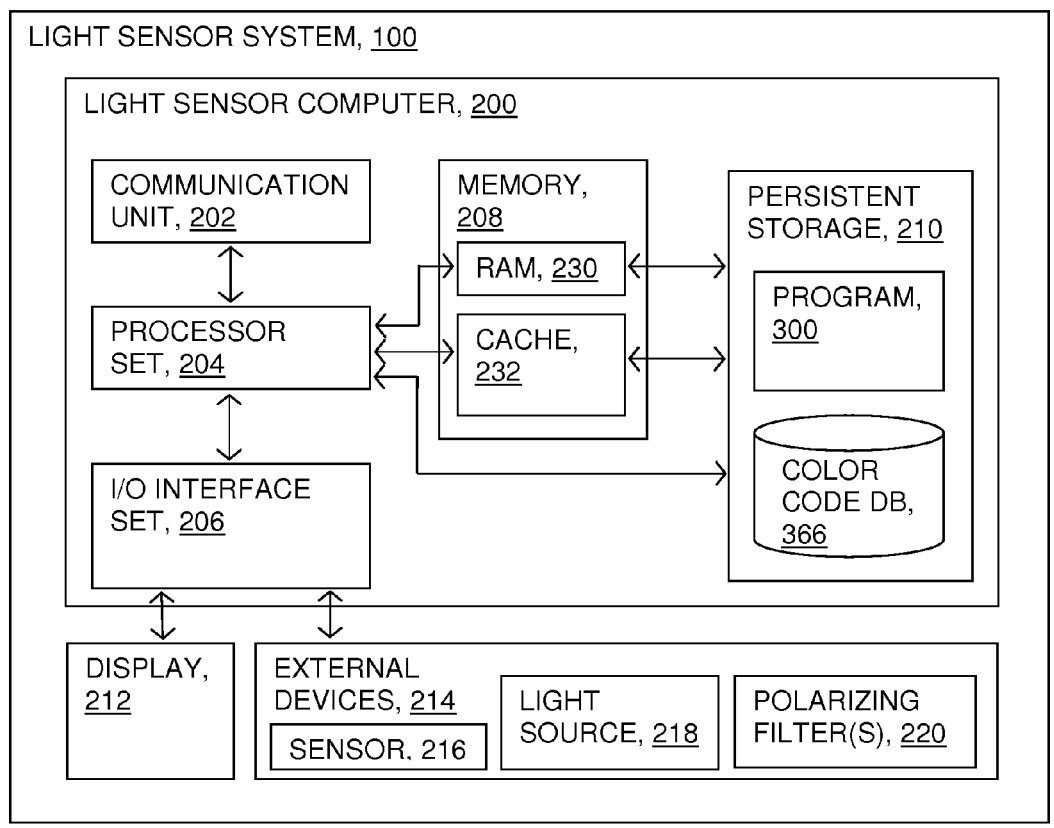
FIG. 1 is a schematic view of a first embodiment of a system according to the present invention.

Polarized light characteristics are detected and mapped to an application, such as product identification. A process of directing a light having particular characteristics, reflecting the directed light through a polarizing filter, and sensing the processed light having particular characteristics is provided. The characteristics of the sensed light is associated with a "color code" that is cross-referenced within a database of color codes. The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium, or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network, and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture, including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions, or acts, or carry out combinations of special purpose hardware and computer instructions.

The present invention will now be described in detail with reference to the Figures. FIG. 1 is a functional block diagram illustrating various portions of light sensor system 100, in accordance with one embodiment of the present invention, including: light sensor computer 200; communication unit 202; processor set 204; input/output (I/O) interface set 206; memory device 208; persistent storage device 210; display device 212; external device set 214; sensor 216; light source 218; polarizing filter(s) 220; random access memory (RAM) devices 230; cache memory device 232; program 300; and color code database 366.

Several portions of system 100 will now be discussed in the following paragraphs.

System 100 may be a laptop computer, tablet computer, netbook computer, personal computer (PC), a desktop computer, a personal digital assistant (PDA), a smart phone, or any programmable electronic device. Program 300 is a collection of machine readable instructions and/or data that is used to create, manage, and control certain software functions that will be discussed in detail below.

System 100 is shown as a block diagram with many double arrows. These double arrows (no separate reference numerals) represent a communications fabric, which provides communications between various components of system 100. This communications fabric can be implemented with any architecture designed for passing data and/or control information between processors (such as microprocessors, communications and network processors, etc.), system memory, peripheral devices, and any other hardware component within a system. For example, the communications fabric can be implemented, at least in part, with one or more buses.

Memory 208 and persistent storage 210 are computer readable storage media. In general, memory 208 can include any suitable volatile or non-volatile computer readable storage media. It is further noted that, now and/or in the near future: (i) external device(s) 214 may be able to supply, some or all, memory for sub-system 100; and/or (ii) devices external to system 100 may be able to provide memory for system 100.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions, and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer readable storage medium that is also part of persistent storage 210.

Communications unit 202, in these examples, provides for communications with other data processing systems or devices external to system 100. In these examples, communications unit 202 includes one or more network interface cards. Communications unit 202 may provide communications through the use of either, or both, physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer readable storage media such as, for example, thumb drives, portable optical or magnetic disks, and memory cards. Software and data used to practice embodiments of the present invention, for example, program 300, can be stored on such portable computer readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the present invention. However, it should be appreciated that any particular program nomenclature herein is used merely for convenience, and thus the present invention should not be limited to use solely in any specific application identified and/or implied by such nomenclature.

Program 300 operates to send and receive emitted light for the purpose of determining a color code associated with the received light. The information corresponding to a given color code is retrieved from color code database 366. Examples of color code related information are: (i) product identification; (ii) component parts information; (iii) instructions; (iv) animal identification; (iv) food characteristics; and/or (v) recycling information.

Some embodiments of the present invention recognize the following facts, potential problems and/or potential areas for improvement with respect to the current state of the art: (i) miniaturization of laser photo diodes allows manufacturing of small and powerful light scanners; (ii) nanomaterial research combines color reflection and the change of polarization during surface reflection; (iii) pigments with nano-materials that clearly produce a pre-determined polarization outcome may be applied to some embodiments of the present invention; (iv) reduced color tag size, while maintaining accurate color reading results from a reasonable distance will support implementation of some embodiments of the present invention; (v) highly efficient polarization filters used at the scanner sensor will support implementation of some embodiments of the present invention; (vi) efficient polarization filters integrated into the design of the reflected-light receiver chip will support implementation of some embodiments of the present invention; (vii) manufacturing an RGB sensor of very tiny size will support implementation of some embodiments of the present invention; (viii) produce a colored reading indicator of the full RGB light spectrum that illustrates the color of the tag will support implementation of some embodiments of the present invention; (ix) reducing an "Arduino" board to a miniature size that fits into a pen-styled housing will support implementation of some embodiments of the present invention; and/or (x) creating an industrial design project for a handy and stylish enclosure, a "pen-like housing," will support implementation of some embodiments of the present invention.

Figure 2:
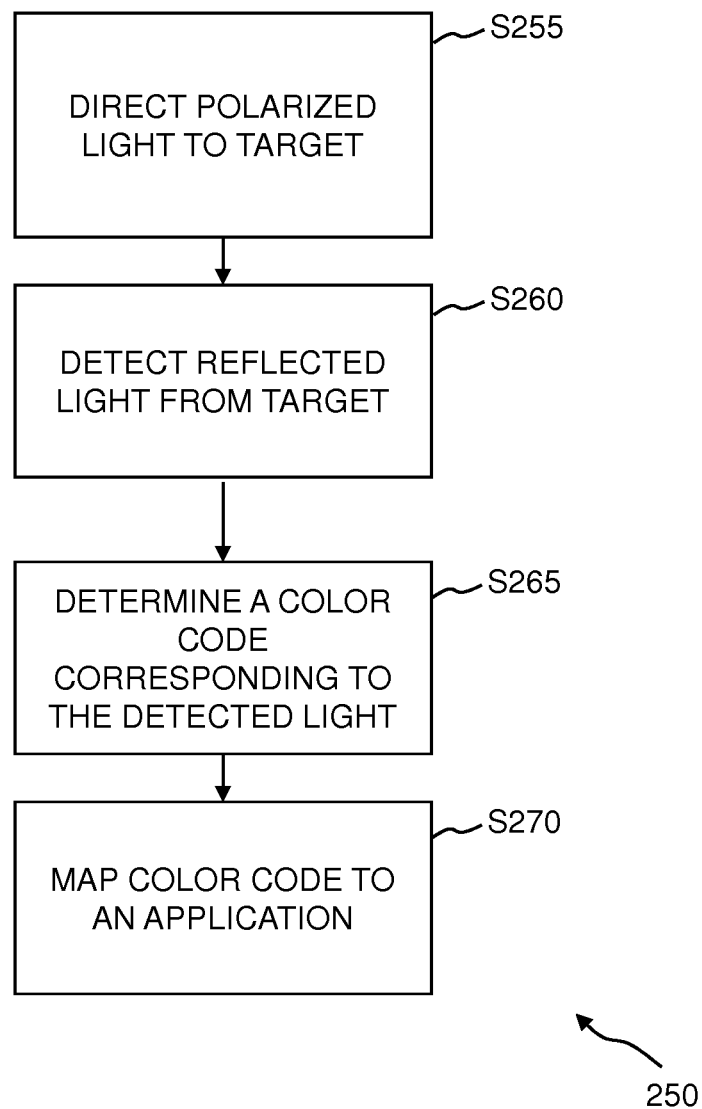
FIG. 2 is a flowchart showing a method performed, at least in part, by the first embodiment system.
Figure 3:
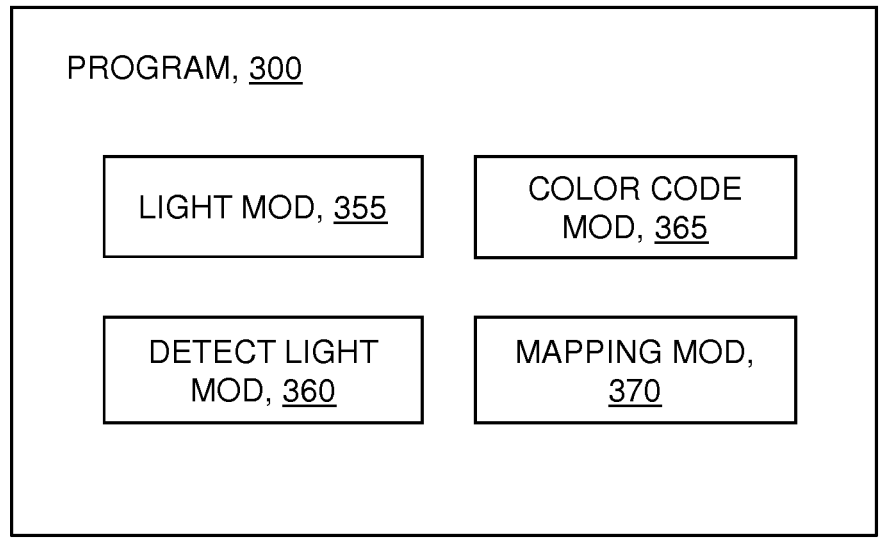
FIG. 3 is a schematic view of a machine logic (for example, software) portion of the first embodiment system.

FIG. 2 shows flowchart 250 depicting a first method according to the present invention. FIG. 3 shows program 300 for performing at least some of the method steps of flowchart 250. This method and associated software will now be discussed, over the course of the following paragraphs, with extensive reference to FIG. 2 (for the method step blocks) and FIG. 3 (for the software blocks).

Processing begins at step S255, where light module 355, emits light from light source 218 through polarizing filter(s) 220 such that polarized light is directed to a target area, or color tag (not shown). In this example, the light source is light emitting diode (LED) and the emitted light is directed toward the target area. Alternatively, light is emitted by an incandescent light. Alternatively, light is emitted in another manner known in the art, such as through gas discharge lamps (neon lamps), lasers, fluorescent lights, and/or halogen lights. Alternatively, the light source is located in a pre-determined position and the target area is placed into the emitted light. In this embodiment, locating the target area within the emitted light is performed by an automated machine. Alternatively, a human user sees that the target area is exposed to the emitted light. The light directed to the target area is polarized according to a particular design. In this example, light polarization characteristics are known at light emission.

Processing proceeds to step S260, where detect light module 360, detects, with light sensor 219, polarized light reflected from the target area. The target area polarizes the light directed to it. In this embodiment, the target area is a plastic film having light polarizing surface characteristics that reflects a certain color when lighted by a polarized light source. Alternatively, the target area is modified with a nanomaterial that has light polarizing characteristics that reflects a certain color when lighted by a white non-polarized light source. Alternatively, the target area is a region of colored ink that reflects a certain color when certain polarized light is directed to its surface. Regardless of the type of light directed to the target area, the reflected light is polarized according to a predetermined design, such that detection of the reflected polarized light is significant.

As discussed above, some embodiments of the present invention emit white light that is polarized during reflection of the light over the target area. Alternatively, the light source emits light having a pre-defined polarization characteristic(s) such that the reflected light has pre-determined characteristics according to the design of the identification tag, or information tag, when reflecting the light having a pre-defined polarization characteristic(s). Color reflection in the identification tag, or target area, is triggered by a surface pigment that produces an RGB color code reading. In this embodiment, the target area is a small colored spot of approximately one square millimeter that is painted over the surface of the object to be identified. Further, in this embodiment, the emitted light originates from a white laser source that combines three lasers diodes, giving the reader a wider spectra.

Some embodiments of the present invention use an electronic sensor, such as sensor 216, for high-accuracy RGB code reading that acts in a large color spectrum. The reading from the sensor is both corrected and determined by computing algorithm. Further, in some embodiments of the present invention, eventual deviations are adjusted in the color spectral readings.

Some embodiments of the present invention produce light polarization with a coating on the information tag area, or target area. The coating, such as a plastic film or reflective surface, differentiates the tag area from the underlying material. The set of polarized light characteristics identifies the painted surface as a target area. In some embodiments, the coating is a nanomaterial surface structure. Polarized light characteristics may include: (i) color; (ii) linear direction; (iii) circular direction; (iv) elliptical direction; (v) intensity; (vi) angle; (vii) direction of propagation; (viii) amplitude; and/or (ix) phase.

Some embodiments of the present invention invoke an active detection process, or scanning process, that supports tag-based information by: (i) direct object viability; and (ii) reflection of certain emitted light. When the emitted light strikes the target area, the reflected light crosses a polarization filter adjacent the target area. In that way, unwanted light spectrum reflected by other sources near the target area is reduced. For example, a surface of an underlying material will reflect unwanted light spectrum with respect to the reflected light from the target area. The polarization filter located adjacent, or nearby, the target area reduces the reflection of unwanted light so that only a single pre-determined color corresponding to identifying information is reflected back from the target area.

Processing proceeds to step S265, where color code module 365 determines a color code that corresponds, according to color code database 366, to the light detected by light sensor 216. The characteristics of the light, such as the spectral information, is identified by the sensor and transmitted to the color code module.

In this example, light sensor system 100 is in the form similar to that of a pen. It may be referred to as a color reader pen. Alternatively, the sensor system is separated into two, or more, components such that the light source is physically separated from the light sensor, and so forth. The two, or more, components may communicate over a network in a wired and/or wireless environment.

Further, in this embodiment, the detected color is displayed in a translucent plastic ring, which is an integrated part of the sensor casing. Also, the digital code, a red-green-blue (RGB) color code, is transmitted to a mobile device (not shown) by Bluetooth communication. (Note: the term "BLUETOOTH" may be subject to trademark rights in various jurisdictions throughout the world and are used here only in reference to the products or services properly denominated by the marks to the extent that such trademark rights may exist.) Alternatively, no color is displayed. Alternatively, the color is displayed on a display device electrically connected to the sensor. Alternatively, the digital code for the color is transmitted over a network (not shown) by connecting the sensor to a USB cable interface.

Processing proceeds to step S270, where mapping module 370 maps the color code, determined in step S265, to an application according to color code database 366.

In one exemplary embodiment, a color tag is made of a colored spot having a surface area of one square millimeter. The color reading is accomplished in the entire light spectrum with three parallel sensors red-green-blue (RGB). The RGB color is identified within a reasonable tolerance and is mapped to the detected color code. For example, to mention an application scenario, the detected color is mapped to a list of trash categories with approximately 200 types of numeric codes. The final product, in this embodiment, is a portable RGB sensor packed into a pen-like device capable of connecting to a cell phone or a tablet through Bluetooth technology. Alternatively, the device connects to peripheral devices via a USB cable interface. In this exemplary embodiment, the sensor is integrated into a pen-like case including: (i) a signaling color ring-like component for visual feedback; (ii) a group of three LEDs; (iii) a translucent ring, confirming successful data acquisition and/or the status of the data acquisition; and (iv) reading from the color tag.

Some embodiments of the present invention provide for color detection from reflections of very small tags, or tag areas, where the information tag is sensitive to certain light polarization characteristics. That is, light sources with white, or unmatched polarization, are filtered at the light source so that the light striking the identification tag is polarized according to a pre-determined design.

One use case for an information tag is where a tag is placed on a clear plastic bottle containing a commercial product. The tag does not change the appearance of the bottle when viewed by the human eye. When a color reader pen directs polarized light at the tag, it reads the reflected polarized light from the tag. The identified color is cross-referenced to a color code, which links to corresponding retail information for the product inside the bottle.

Some embodiments of the present invention use attenuation of light readings reflected by the color tag. Further, some embodiments use light polarization characteristics at light emission, during light reflection at the tag surface, and for ambient light filtering at the receiving color sensor for convey information in a detected color. Some embodiments of the present invention use an emitting light source having known characteristics.

Some embodiments of the present invention provide a method for using information received from an identification tag in real time. The method includes: scanning a predetermined area of an object representative of the identification tag with an optical scanner wherein a light emitted by the optical scanner illuminates a portion of the predetermined area and crosses a polarization filter to reduce an unwanted light spectrum reflected by other sources, receiving a reflection of the light emitted through the polarization filter at a receiver associated with the optical scanner, wherein the receiver is sensitive to a predetermined range of light polarization characteristics of the light reflected, identifying spectral information in the light reflected, identifying a color code within a predetermined tolerance contained within spectral information identified, and mapping the color code identified to an application.

Some embodiments of the present invention may include one, or more, of the following features, characteristics and/or advantages: (i) a color tag is a spot that may have a surface area of one square millimeter; (ii) the color tag is very low cost when compared to conventional bar code printing; (iii) the color tag works on a smaller surface area when compared to the surface area requirement of a bar code; (iv) some embodiments of the color detector pen do not use a digital display; (v) automated color reading process in real time; (vi) a small error ratio, by including in color code detection system that involves the detection and filtering of polarized light; (vii) a machine readable tag applicable on a large color spectra including ultraviolet light, visible light, and/or infrared light; (viii) the very small surface area of the color tag allows the industry to identify much smaller objects using the tag (such as a coin cell battery); (ix) uses less ink and pigments for tag printing than conventional bar code systems; (x) the color tag does not affect the material recycling process; (xi) stands up to a harsh environment; (xii) versatile use for numerous applications; (xiii) employs a small tag for discrete use with a non-conspicuous appearance printed over the product surface of any type of material; (xiv) the color pen interacts easily with smart devices, appliances, and/or mobile devices via bluetooth communication and/or USB interfaces; (xv)

some embodiments require line-of-sight between the information tag and the color detection pen; and/or (xvi) some embodiments have a limited reading distance between the information tag and the color sensor (for example, a maximum distance of 20 inches may be implemented).

Some helpful definitions follow:

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

User/subscriber: includes, but is not necessarily limited to, the following: (i) a single individual human; (ii) an artificial intelligence entity with sufficient intelligence to act as a user or subscriber; and/or (iii) a group of related users or subscribers.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A method comprising:
    detecting, by an optical scanner device, a first light emission through a polarization filter, the first light emission having a first set of characteristics reflected from a target area on a surface of an object;
    determining, by the optical scanner device, a color code based, at least in part, on the first light emission;
    mapping the color code to a corresponding application including at least one of: component parts information instructions, food characteristics, and recycling information; and
    providing or displaying information regarding the application to a device via communications hardware,
    wherein:
    at least the detecting and determining steps are performed by computer software running on computer hardware of the optical scanner device; and
    the first light emission is a polarized reflection from the target area of a second light emission having a second set of characteristics that are different from the first set of characteristics, the second light emission being emitted by the optical scanner device on to the target area.

2. The method of claim 1, further comprising:
    directing the second light emission such that the target area reflects the second light emission.

3. The method of claim 1, further comprising:
    mapping the color code to a set of product identification data.

4. The method of claim 1, wherein the first set of characteristics includes a pre-determined polarization.

5. The method of claim 1, wherein detecting the first light emission is performed, at least in part, by a light receiver sensitive to a pre-determined range of light polarization characteristics.

6. The method of claim 1, wherein determining a color code includes identifying spectral information of the first light emission.

7. The method of claim 1, wherein the target area includes at least one selected from the group consisting of:
    a nanomaterial; and
    a plastic film.

8. The method of claim 7, wherein the polarization filter is adjacent to the target area.

9. A computer program product implemented within an optical scanner, the computer program product comprising a computer readable storage medium having stored thereon:
    first program instructions programmed to detect a first light emission through a polarization filter having a first set of characteristics reflected from a target area on a surface of an object;
    second program instructions programmed to determine a color code based, at least in part, on the first light emission;
    third program instructions to map the color code to a corresponding application including at least one of: product identification, component parts information instructions, food characteristics, and recycling information; and
    fourth program instructions to provide or displaying information regarding the application to a device via communications hardware,
    wherein:
    the first light emission is a polarized reflection from the target area of a second light emission having a second set of characteristics that are different from the first set of characteristics, the second light emission being emitted by the optical scanner device on to the target area.

10. The computer program product of claim 9, further comprising:
    third program instructions programmed to direct the second light emission such that the target area reflects the second light emission.

11. The computer program product of claim 9, further comprising:
    third program instructions programmed to map the color code to a set of product identification data.

12. The computer program product of claim 9, wherein the first set of characteristics includes a pre-determined polarization.

13. The computer program product of claim 9, wherein detecting the first light emission is performed, at least in part, by a light receiver sensitive to a pre-determined range of light polarization characteristics.

14. The computer program product of claim 9, wherein determining a color code includes identifying spectral information of the first light emission.

15. An optical scanner system comprising:
    a processor(s) set; and
    a computer readable storage medium;
    wherein:
    the processor set is structured, located, connected, and/or programmed to run program instructions stored on the computer readable storage medium; and the program instructions include:

first program instructions programmed to detect a first light emission through a polarization filter having a first set of characteristics reflected from a target area on a surface of an object;

second program instructions programmed to determine a color code based, at least in part, on the first light emission;

third program instructions to map the color code to a corresponding application including at least one of: product identification, component parts information instructions, food characteristics, and recycling information; and fourth program instructions to provide or displaying information regarding the application to a device via communications hardware, wherein:

the first light emission is a polarized reflection from the target area of a second light emission having a second set of characteristics that are different from the first set of characteristics, the second light emission being emitted by the optical scanner system on to the target area.

16. The computer system of claim 15, further comprising:
third program instructions programmed to direct the second light emission such that the target area reflects the second light emission.

17. The computer system of claim 15, further comprising:
third program instructions programmed to map the color code to a set of product identification data.

18. The computer system of claim 15, wherein the first set of characteristics includes a pre-determined polarization.

19. The computer system of claim 15, wherein detecting the first light emission is performed, at least in part, by a light receiver sensitive to a pre-determined range of light polarization characteristics.

20. The computer system of claim 15, wherein determining a color code includes identifying spectral information of the first light emission.

* * * * *